United States Patent [19]

Grüning et al.

[11] Patent Number: 5,023,246

[45] Date of Patent: Jun. 11, 1991

[54] BETAINE GROUP-CONTAINING DERIVATIVES OF CARBOXYMETHYLCELLULOSE, THEIR SYNTHESIS AND THEIR USE IN COSMETIC PREPARATIONS

[75] Inventors: Burghard Grüning; Klaus Hoffmann; Götz Koerner; Hans-Joachim Kollmeier, all of Essen, Fed. Rep. of Germany

[73] Assignee: Th. Goldschmidt AG, Essen, Fed. Rep. of Germany

[21] Appl. No.: 353,399

[22] Filed: May 17, 1989

[30] Foreign Application Priority Data

Jun. 13, 1988 [DE] Fed. Rep. of Germany ....... 3820029

[51] Int. Cl.$^5$ .......................... A61K 7/00; C08B 1/00; C08B 3/00; C08B 11/00
[52] U.S. Cl. ..................... 514/57; 514/880; 514/881; 536/30; 536/32; 536/43; 424/70
[58] Field of Search .................. 514/57, 880, 881; 536/30, 43, 32; 424/70, 71

[56] References Cited

U.S. PATENT DOCUMENTS

| | | | |
|---|---|---|---|
| 3,472,840 | 10/1969 | Stone et al. | 536/43 |
| 4,577,013 | 3/1986 | Merz et al. | 536/43 |
| 4,617,385 | 10/1986 | Namikoshi et al. | 536/43 |
| 4,710,374 | 12/1987 | Grollier et al. | 514/881 |

FOREIGN PATENT DOCUMENTS

| | | | |
|---|---|---|---|
| 49-18981 | 2/1974 | Japan . | |
| 55-43165 | 3/1980 | Japan . | |
| 58-116409 | 7/1983 | Japan | 514/880 |

*Primary Examiner*—Ronald W. Griffin
*Assistant Examiner*—Everett White
*Attorney, Agent, or Firm*—Toren, McGeady & Associates

[57] ABSTRACT

Betain group-containing derivatives of carboxymethylcellulose are disclosed. They are characterized in that all or a portion of the carboxymethyl groups are or is replaced by groups of the general formula

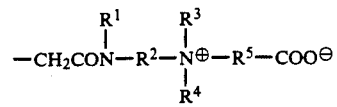

wherein
$R^1$ is hydrogen or methyl group,
$R^2$ is a divalent aliphatic hydrocarbon group with 2 to 5 carbon atoms,
$R^3$, $R^4$ is an alkyl group with 1 to 4 carbon atoms,
$R^5$ is a divalent aliphatic hydrocarbon group with 1 to 10 carbon atoms, with the proviso that, on the average, at least 0.1 betaine groups are contained for each anhydroglucose unit of the polymeric molecule.

Also, a method for the synthesis of these compounds and their use in cosmetic preparations, especially for the care of hair, are disclosed. In addition, novel derivatives of carboxymethylcellulose with tertiary amino groups are taught as intermediates. In these derivatives, all or a portion of these groups are or is replaced by groups of the general formula

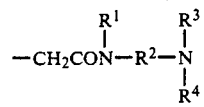

in which the substituents $R^1$, $R^2$, $R^3$ and $R^4$ have the above meaning, with the proviso that, on the average, at least 0.1 tertiary amino groups are contained per anhydroglucose unit of the polymeric molecule.

10 Claims, No Drawings

BETAINE GROUP-CONTAINING DERIVATIVES OF CARBOXYMETHYLCELLULOSE, THEIR SYNTHESIS AND THEIR USE IN COSMETIC PREPARATIONS

FIELD OF INVENTION

The invention is directed to betaine group-containing derivatives of carboxymethylcellulose, as well as to a method for the synthesis of these compounds. Considered from another aspect, the invention is concerned with the use of these derivatives in cosmetic preparations, especially for the care of the hair.

The invention furthermore is directed to tertiary amino group-containing derivatives of carboxymethylcellulose as intermediates in the synthesis of betaine group-containing derivatives of carboxymethylcellulose.

BACKGROUND INFORMATION AND PRIOR ART

Betaine group-containing derivatives of hydroxyethylcellulose are known from the art. However, these products do not have satisfactory properties when used in cosmetics, especially when used for the preparation of products for the care of hair. It is a further disadvantage of these products that, for their synthesis, reactants are used, which are not safe physiologically and the complete removal of which from the end product is not readily possible or requires measures, which make the economic use of the compounds impossible.

The Japanese published application No. 80-43 165 is named as belonging to this state of the art. This application claims amphoteric derivatives of hydroxyethylcellulose, these derivatives being characterized by at least 50 structural units of the general formula

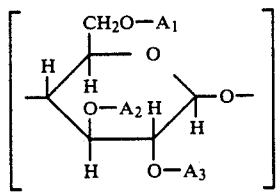

In this general formula
$A_1$ represents the group $-(C_2H_4O-)_pX_1$
$A_2$ represents the group $-(C_2H_4O-)_qX_2$
$A_3$ represents the group $-(C_2H_4O-)_rX_3$ $X_1$, $X_2$ and $X_3$ being either a hydrogen atom or an amphoteric group of the general formula

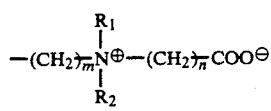

In this amphoteric group, $R_1$ and $R_2$ are a methyl or an ethyl group, m is a whole number from 1 to 6 and n is a whole number from 1 to 2, p, q and r=0 or a whole number not less than 1. The average number of moles of oxyethylene groups per structural unit is 0.5 to 3.0 and the average degree of substitution by amphoteric groups per structural unit is 0.02 to 1.0. It is evident from this description of the formula that the betainic group is linked over ether bonds to the cellulose backbone.

Pursuant to the Japanese application No. 80-43 165, these compounds are synthesized by, expressed in a simplified fashion, at first reacting an appropriate hydroxyethylcellulose with dialkylaminoalkyl halides of the general formula

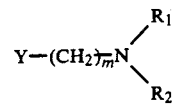

in the presence of alkali. In the above formula, Y is a halogen atom and the $R_1$ and $R_2$ groups and the m subscript have the above meaning given. The intermediate obtained is then reacted with a monohalogencarboxylic acid or acrylic acid in the presence of alkali.

For various reasons, this method has proven to be disadvantageous. For instance, the dialkylaminoalkyl halide, used in the first step of the method, is an alkylating agent, which is not entirely safe physiologically and which should not remain in the product, especially if the end products are used in cosmetics. However, it is practically impossible to remove dialkylaminoalkyl halide quantitatively.

A further disadvantage consists therein that the tertiary amine, formed in the first step, reacts more readily with further dialkylaminoalkyl halide than do the still unreacted hydroxyethyl groups of the hydroxyethylcellulose. In a side reaction, as a result of the addition reaction with a second dialkylaminoalkyl halide, this then leads to the formation of derivatives with quaternary amino groups, which are present in the end product in addition to the derivatives with betainic groups. Through the formation of these by-products, however, the compatibility of the products with anionic surfactants is reduced appreciably. This is of disadvantage in the application, since products for the care of hair in many cases contain anionic surfactants as well. The desired advantage in the application of the improved compatibility of compounds containing betaine groups is thus reduced or canceled.

Betaine group-containing derivatives of hydroxyethylcellulose are also disclosed, under certain assumptions, in the U.S. Pat. No. 3,472,840. In this U.S. Patent, a cellulose ether of the general formula

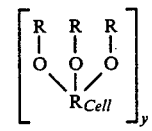

which contains a quaternary nitrogen, is claimed. The $R_{Cell}$ group is an anhydroglucose unit, y is a whole number with a value from 50 to 20,000 and each R represents a group of the general formula

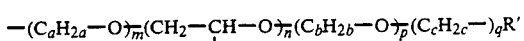
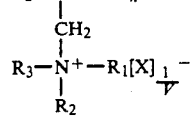

in which a is a whole number with a value of 2 to 3,
b is a whole number with a value of 2 to 3,
c is a whole number with a value of 1 to 3,
m is a whole number with a value of 0 to 10,
n is a whole number with a value of 0 to 3,
p is a whole number with a value of 0 to 10,
q is a whole number with a value of 0 to 1,
R' is selected from a group consisting of

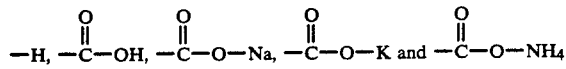

with the proviso that R'=H when q=0.

R₁, R₂ and R₃ in each case represent an alkyl, aryl, aralkyl, alkaryl, cycloalkyl, alkoxyalkyl or alkoxyaryl group with up to 10 carbon atoms. V is a whole number, which corresponds to the valence of X (to shorten it and to make it more understandable, some conditions have been disregarded in this citation).

In this U.S. Patent, the limiting case is mentioned, in which the anion X can be omitted completely or partly when R' is a carboxyl group, which forms an internal salt with the quaternary ammonium group. In this case, a betainic structure is present. If the anion X is displaced only partly, the disadvantages are observed again which are inherent in products in which quaternary ammonium groups and betaine groups are present side by side, namely a poor or inadequate compatibility with anionic surfactants. Even in the limiting case of the complete omission of the x anion, these compounds are derivatives of hydroxyethyl or hydroxypropyl ether.

Izv. Vyssh. Uchebn. Zaved. Khim. Khim. Tekhnol. 26 (1983) 1480 to 1482 discloses a modification of cellulosic textile fibers by an appropriate chemical reaction. This modification is such that the textile fibers have betaine groups in order to strive for certain property improvements. However, the products involved are insoluble in water. For this reason alone, they cannot be used in cosmetics.

OBJECTS OF THE INVENTION

It is an object of the present invention to provide betaine group-containing cellulosic products, which can be used especially in cosmetic preparations for the care of hair and, at the same time, have improved hair-care properties. The products shall have an improved compatibility with anionic surfactants, show good solubility properties and dissolve without producing pronounced gel-like intermediate states. More particularly, when used on hair, the novel products shall bring about improved gloss, handle and combability. The substantivity of the products shall be so balanced, that any accumulation of the active ingredients on the hair, even after repeated application, is avoided.

Another object is to provide a simple method to synthesize the novel products.

SUMMARY OF THE INVENTION

It has now been ascertained that betaine group-containing derivatives of carboxymethylcellulose have this profile of properties. One aspect of the invention therefore are betaine group-containing derivatives of carboxymethylcellulose with the characteristic feature, that all or a portion of the carboxymethyl groups are or is replaced by groups of the general formula

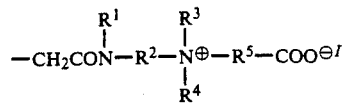

wherein
R¹ is a hydrogen or methyl group
R² is a divalent aliphatic hydrocarbon group with 2 to 5 carbon atoms,
R³, R⁴ is an alkyl group with 1 to 4 carbon atoms,
R⁵ is a divalent aliphatic hydrocarbon group with 1 to 10 carbon atoms,
with the proviso that, on the average, at least 0.1 betaine groups are present for each anhydroglucose unit of the polymeric molecule.

Preferred are those derivatives of carboxymethylcellulose, which, on the average, have 0.3 to 0.8 and especially 0.3 to 0.6 betaine groups per anhydroglucose unit.

The number of anhydroglucose units in the polymeric molecule should be about 400 to 10,000.

In Formula I, R¹ represents a hydrogen or methyl group. Preferably, R¹ is a hydrogen group.

R² is a divalent aliphatic hydrocarbon group with 2 to 5 carbon atoms. This alkylene group optionally many be branched. However, linear alkylene groups and especially those with 2 to 4 carbon atoms are preferred. Examples of those R² groups are

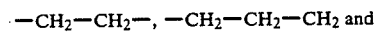

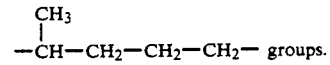

The R³ and R⁴ groups may be the same or different and represent alkyl groups with 1 to 4 carbon atoms. The methyl group is preferred.

R⁵ is a divalent aliphatic hydrocarbon group with 1 to 10 carbon atoms; preferably, it is a linear, divalent, aliphatic hydrocarbon group. The DCH₂— group is especially preferred.

A further aspect of the invention is a method for the synthesis of the inventive compounds. This inventive method is carried out in three principal steps. According to a simplified description, alkali salts of the carboxymethylcellulose are esterified with alkyl chloride in the first step; the ester, thus obtained, is converted into a derivative with tertiary amino groups in the second step and the intermediate obtained is alkylated in the third step with formation of the betaine group.

The inventive method thus is characterized in that
(a) an alkali salt of the carboxymethylcellulose is esterified at temperatures of 80° to 170° C., a pressure of 5 to 100 bar and a reaction time of 1 to 24 hours in a known manner with, based on the carboxymethyl groups, a 1- to 10-fold excess of alkyl chloride, the alkyl group of which has 1 to 3 carbon atoms. The excess alkyl chloride is removed from the reaction mixture in a known manner after the esterification,
(b) the ester of the carboxymethylcellulose, thus obtained, is reacted with amines of the general formula

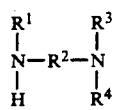

in which R¹, R², R³ and R⁴ are defined as in Formula I, at temperatures of 80° to 150° C., a reaction time of 1 to 10 hours and optionally at an elevated pressure in such amounts, that 1 to 10 moles of amine are used per mole of ester group. After the reaction, the excess amine is removed from the reaction mixture in a known manner, whereupon (c) the derivative of carboxymethylcellulose thus obtained, which contains tertiary amino groups, is reacted at a temperature of 40° to 120° C. and a reaction time of 0.5 to 8 hours with, based on the tertiary amino groups, at least equimolar amounts of the compound X-R⁵-COOM, in which X is a halogen group, M is an alkali or an ammonium ion and R⁵ is as defined in Formula I.

The esterification in the first step is carried out by a known procedure with alkyl chloride, the alkyl group of which has 1 to 3 carbon atoms. Preferably, methyl chloride is used for the esterification. The reaction is carried out at an elevated temperature of 80° to 170° C., a temperature in the range of 80° to 110° C. being preferred. The reaction is carried at an elevated pressure of 5 to 100 bar and preferably at a pressure of 5 to 50 bar. The reaction is completed within 1 to 24 hours, depending on the alkyl chloride used. Yields as high as 95% of the theoretical can be achieved. At least equimolar amounts of alkyl chloride are used. It is advisable to use an excess of alkyl chloride; however, for economic reasons, a more than 10-fold excess is avoided. After the reaction, the excess amount of alkyl chloride is removed in a known manner, preferably by distillation.

In the second step, the alkyl ester of the carboxymethylcellulose, thus obtained, is reacted with amines of the general formula

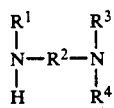

The R¹, R², R³ and R⁴ groups are defined as in Formula I. A reaction temperature, which falls within the range of 80° to 150° C. and preferably within the range of 100° to 140°, is selected. The reaction optionally may be carried out at an elevated pressure, which depends on the boiling point of the amine used. The reaction is concluded within 1 to 10 hours with a yield of about 90%. Per ester group, 1 to 10 moles of the amine are used. The excess amine is removed after the reaction in a known manner. This can be accomplished by filtering the reaction product from the reaction mixture, the precipitation of the reaction product being completed by the addition of polar organic solvents, such as acetone, isopropanol or methanol. Preferably, the reaction is carried in suspension with addition of a neutral, polar, organic solvent such as methanol or isopropanol, in a pressure vessel. Preferably, 1 to 3 moles of amine are used for each ester group. Examples of suitable amines of Formula III are

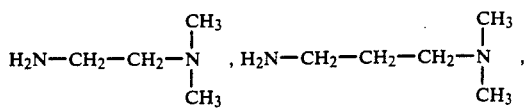

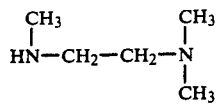

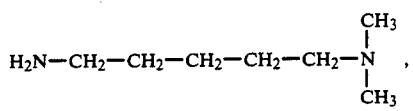

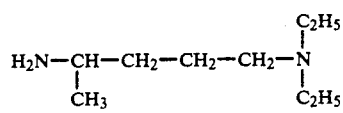

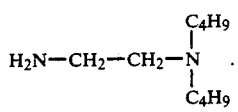

The intermediates obtained in the second step are novel compounds, the properties of which determine the properties of the inventive end products. These novel intermediates, in the form of derivatives of carboxymethylcellulose with tertiary amino groups, therefore are a further aspect of the invention and are characterized in that all or a portion of the carboxymethyl groups are replaced by groups of the general formula

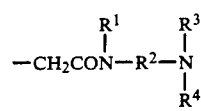

in which the substituents R¹, R², R³ and R⁴ have the meaning given in Formula I, with the proviso that, on the average, at least 0.1 tertiary amino groups are contained per anhydroglucose unit of the polymeric molecule.

These novel intermediates are now reacted in the third step of the inventive method with, based on the tertiary amino groups, at least equimolar amounts of the compound X-R⁵-COOM. Examples of suitable compounds of this formula are Cl—CH₂—COONa, Br—CH₂—CH₂—COONa and BrD(CH₂)₁₀—COOK.

The alkylation reaction with formation of the betaine structure is carried out in a known manner. It should be conducted at temperatures ranging from 40° to 120° C. and preferably from 60° to 100° C.

The reaction of step 3 can be carried out in a 2-phase system, the derivative of the carboxymethylcellulose, which is obtained in the second step, being suspended in a suitable liquid, organic phase, such as methanol. A reaction in an aqueous phase is possible; however, because of the high viscosity of the solution, such a reaction is preferred only if the end product is to be used further, directly in the form of an aqueous solution.

The compounds prepared by the inventive method are to a large extent soluble in cold as well as in warm water without the formation of a gel-like intermediate.

A further aspect of the invention is the use of inventive compounds in cosmetic preparations, especially for the care of hair. The inventive compounds meet the requirements listed above particularly well.

The inventive compounds can be processed together with anionic surfactants without any cloudiness or precipitation being observed. If hair is treated with aqueous preparations of the inventive compounds, it develops the desired gloss and the pleasant, supple, soft handle and is readily combable. The products have proven to be useful especially for the care of damaged hair.

The inventive compounds are then contained in the aqueous preparations in an amount of 0.1 to 2.5% by weight. Skin irritations or hair damage have not been observed with the inventive compounds.

The inventive compounds can, moreover, be used to thicken aqueous solutions or aqueous suspensions. They are suitable for the treatment of textile fibers or of yarns produced therefrom or of sheet-like textile fabrics. A considerable improvement in the handle and a decrease in the electrostatic charge are obtained in this manner. The inventive compounds can furthermore be added to paper pulp during the manufacture of paper. The compounds can furthermore be used to thicken aqueous vehicles or binders.

In the following examples, the synthesis of the inventive compounds is shown. It should be noted that these examples are given by way of illustration and not by way of limitation. Furthermore, the application properties of the compounds are shown in comparison with those of products of the state of the art.

I PREPARATION OF INVENTIVE COMPOUNDS

1. Preparation of Carboxymethylcellulose Methyl Ester (Step (a) of the Method)

(1a) As described in the Japanese publication No. 49-18 981, 30 g of sodium carboxymethylcellulose, with a degree of modification DS=0.9, a saponification number of less than 4 and a purity of 99.5%, the 1% aqueous solution of which has a Brookfield viscosity of approximately 2,000 mPas, and 87 g of chloromethane are heated for 10 hours at 100° C. in a 250 mL autoclave. During this time, a pressure of about 40 bar is developed. Subsequently, the chloromethane is evaporated off. To complete the removal of the chloromethane, the product is heated at 60 mbar to 50° C. A total of 34 g of carboxymethylcellulose methyl ester, mixed with the sodium chloride that is formed as a by-product of the reaction, are obtained. The methyl ester has a saponification number of 225, which corresponds to a 90% conversion of the carboxyl groups.

(1b) In the same way, 30 g of sodium carboxymethylcellulose, with a degree of modification DS of 0.7, a saponification number of less than 4 and a purity of 99.5%, the 1% aqueous solution of which has a Brookfield of about 1,500 mPas, is reacted with chloromethane. The carboxymethylcellulose methyl ester obtained has saponification number of 200, which corresponds to an 86% conversion of the carboxyl groups.

2. Preparation of the Aminamide of Carboxymethylcellulose (Step (b) of the Process)

(2a) The carboxymethylcellulose methyl ester (30 g), obtained by the method of Section (1a), is heated under reflux with stirring for 6 hours with 200 g of dimethylaminopropylamine. The reaction mixture is cooled and 1,000 g of isopropanol are added for the complete precipitation of the reaction product. The carboxymethylcellulose aminamide is isolated by filtering with the help of suction and extracted with isopropanol in a Soxhlet apparatus. The amine nitrogen content of the product is determined by titration to be 2.2%. This corresponds to a 60% conversion. The product is readily soluble in water.

(2b) Carboxymethylcellulose methyl ester (30 g), obtained according to the method of Section (1a), is heated in a 250 mL laboratory autoclave together with 24 g of dimethylaminopropylamine and 100 g of methanol with stirring for 1 hour at 150° C., a pressure of 18 bar developing. After cooling, the product is filtered off with suction and washed with methanol. The amine nitrogen content after drying is determined by titration to be 3.4%. This corresponds to a 92% conversion based on the ester groups. The $^1$H-NMR spectrum, recorded in $D_2O$, shows the signal of the methyl substituents of the tertiary amino group at 2.4 ppm as the characteristic peak.

(2c) As described in Section (2b), 30 g of the same carboxymethylcellulose methyl ester are reacted with 21 g of dimethylaminoethylamine. The amine nitrogen content of the carboxymethylcellulose aminamide obtained is 3.3%. This corresponds to an 85% conversion of the ester groups.

(2d) In the same way, 30 g of the same carboxymethylcellulose methyl ester are reacted with 24 g N,N,N'-trimethylethylenediamine. The amine nitrogen content of the carboxymethylcellulose aminamide obtained is 2.9%. This corresponds to a 79% conversion of the ester groups.

(2e) In the same way 30 g of the same carboxymethylcellulose methyl ester are reacted with 37 g of 1-diethylamino-4-aminopentane. The amine nitrogen content of the carboxymethylcellulose aminamide obtained is 2.6%. This corresponds to a 83% conversion of the ester groups.

(2f) In the same way, 30 g of the same carboxymethylcellulose methyl ester are reacted with 40 g of dibutylaminoethylamine. The amine nitrogen content of the carboxymethylcellulose aminamide obtained is 2.4%. This corresponds to an 80% conversion of the ester groups.

(2g) The carboxymethylcellulose methyl ester (30 g), obtained according to the method of Section (1b), is heated for 1 hour with stirring to 150° C. in a 250 mL laboratory autoclave together with 24 g of dimethylaminopropylamine and 100 g of isopropanol, a pressure of about 10 bar developing. After cooling, the product is filtered off with suction and washed with isopropanol. The amine nitrogen content after drying is determined to be 2.4%. This corresponds to a 65% conversion of the ester groups. The Brookfield viscosity of a 2% aqueous solution of the carboxymethylcellulose aminamide prepared is 500 mPas.

3. Conversion of the Aminamide of the Carboxymethylcellulose to the Betaine (Step (c) of the Method)

(3a) The carboxymethylcellulose aminamide (25 g), obtained by the method of Section (2b), is suspended in 200 g of isopropanol and 50 g of water and mixed with a solution of 7.1 g of sodium chloroacetate in 14 g of water. The batch is stirred intensively for 6 hours at 60° C. The product is filtered off with suction, washed with isopropanol/water and dried. In the zwitterionic derivative of cellulose obtained, the amine nitrogen is no longer detectable unambiguously by titration of an aqueous solution of the polymer with perchloric acid.

The $^1$H-NMR spectrum, recorded in $D_2O$, shows as characteristic peaks the signals of the methyl substituents of the tertiary amino group at $\delta=2.9$ ppm and of the corresponding quaternized group at $\delta=3.2$ ppm. The intensity ratio of these signals indicates an approximately 85% conversion. Starting out from a carboxymethylcellulose with a degree of substitution DS=0.9, a 90% conversion during the esterification reaction and a 92% conversion during the amidation reaction, a degree of substitution DS=approx. 0.63, based on the betainic groups, is obtained.

(3b) As described in Section (3a), 25 g of carboxymethylcellulose aminamide, the synthesis of which is described in Section (2c), is reacted with 6.9 g of sodium chloroacetate. In the zwitterionic cellulose derivative obtained, the amine nitrogen can no longer be detected unambigously by titration with perchloric acid.

(3c) As described in Section (3a), 25 g of carboxymethylcellulose aminamide, the synthesis of which is described in Section (2d), is reacted with 6.1 g of sodium chloroacetate. In the zwitterionic cellulose derivative obtained, the amine nitrogen can no longer be detected unambiguously by titration with perchloric acid.

(3d) As described in Section (3a), but with a reaction time increased to 24 hours, 25 g of carboxymethylcellulose aminamide, the synthesis of which is described in Section (2e), is reacted with 6 g of sodium chloroacetate. In the zwitterionic cellulose derivative obtained, the amine nitrogen can no longer be detected unambiguously by titration with perchloric acid.

(3e) As described in Section (3d), 25 g of carboxymethylcellulose aminamide, the synthesis of which is described in Section (2f), is reacted with 6 g of sodium chloroacetate. In the zwitterionic cellulose derivative obtained, the amine nitrogen no longer can be detected unambiguously by titration with perchloric acid.

(3f) Carboxymethylcellulose aminamide (25 g), the synthesis of which is described in Section (2b), is suspended in 200 g of isopropanol and 50 g of water and mixed with 10.7 g of sodium $\beta$-bromopropionate. The batch is stirred intensively for 12 hours at 60° C. The product is subsequently filtered off and dried. The bromide content of the product is 11%.

(3g) Carboxymethylcellulose aminamide (25 g), the synthesis of which is described in Section (2b), is dissolved in 650 mL of water, mixed with 7.1 g of sodium chloroacetate, adjusted with NaOH to a pH of 10 and heated to 60° C. The pH of the solution is followed. After 12 hours, the pH no longer changes and the reaction is completed. The chloride value is 0.3% Cl$^-$.

II

1. Dressing hair with inventive betainic cellulose derivatives and betainic and cationic cellulose derivatives of the state of the art.

The following cellulose derivatives are investigated with respect to their conditioning effect on hair:

Cellulose derivatives A, B and C are products similar to those of the state of the art and are not of the invention.

A: A hydroxyethylcellulose, modified with 3-chloro-2-hydroxypropyltrimethylammonium chloride, having a low viscosity and corresponding to U.S. Pat. No. 3,472,840. The product has a nitrogen content of 1.7% and is commercially available under the name of Polymer JR 400.

B: A hydroxyethylcellulose, which is modified with 3-chloro-2-hydroxypropyltrimethylammonium chloride, having a higher viscosity and corresponding to U.S. Pat. No. 3,472,840. The product has a nitrogen content of 1.7% and is commercially available under the name of Polymer JR 30 M.

C: A hydroxyethylcellulose, modified with 2-chloroethyldiethylamine and sodium chloroacetate and corresponding to Example 1 of the Japanese publication No. 80-43 165.

Cellulose derivatives D, E, F and G are inventive cellulose derivatives with betaine groups.
D Synthesis described in Section (3a)
E Synthesis described in Section (3b)
F Synthesis described in Section (3c)
G Synthesis described in Section (3d)

Aqueous (0.1%) solutions of the cellulose derivatives A to G are prepared.

Chinese fine hair, 15 cm long, is bleached with a commercial bleach for 1 hour according to the directions provided and subsequently dried. The care rinse, enclosed with the bleaching agent, is not used. The now lightened and damaged hair is tied into strands of about 1 g each. The strands are left for 10 minutes at 30° C. in the solutions described above. Subsequently, they are rinsed thoroughly for 3 minutes in luke-warm running water, dried 12 hours in air and combed. In each case, 3 strands of hair are treated with each of the solutions.

With regard to handle and combability, there are clear differences between the differently treated strands of hair. On the basis of these differences, the cellulose derivatives A to G can be arranged in a sequence. The cellulose derivatives, which lead to the best result, are named first. The following results are obtained:

Wet Combability: D=E>G>A>F>C>B>> bleached, untreated hair
Dry Combability: G>D>F>E>C>B>A>> bleached, untreated hair
Handle: E>G>D>F>C>A=B>> bleached, untreated hair According to these results, the inventive compounds D and G proved to be particularly suitable for this application.

2. Treatment of hair with shampoo preparations, which contain betainic cellulose derivatives of the invention and cationic and betainic cellulose derivatives of the state of the art.

With the cellulose derivatives A to G, described under II/1, shampoo preparations are produced, which consist of 1% cellulose derivative, 20% sodium lauryl sulfate, 4% sodium chloride and 75% water. In addition, a shampoo preparation, consisting of 20% sodium lauryl sulfate, 4% sodium chloride and 76% water, is prepared for comparison.

Chinese fine hair is bleached and tied as described.

In each case, one strand of hairs is moistened under luke-warm, running water. The wet hair is washed for 10 minutes with a pea-size amount of the respective shampoo preparation, then rinsed thoroughly with luke-warm, running water and dried with the hair drier. In each case, 3 hair strands are treated in the manner described with each of the shampoo preparations.

There are clear differences with respect to handle and combability. On the basis of the results, the cellulose derivatives can be arranged in the following order:

Wet Combability: D>G>A=C=E=F>B>> bleached, untreated hair

Dry Combability: D>E>G>F>A=C>B>> bleached, untreated hair

Handle: E>D>G>C>F>A=B>> bleached, untreated hair

The inventive cellulose derivatives D, E and G have proven to be particularly suitable for this application and even the cellulose derivative F differs clearly with respect to combability from the cellulose derivatives used for comparison.

IV Thickening Aqueous Surfactant Solutions

In this example, the thickening effect of an inventive cellulose betaine in surfactant solutions and the compatibility of this cellulose betaine with an anionic (sodium lauryl sulfate) as well as with a cationic (coconut dimethylbenzylammonium chloride) surfactant is shown. For comparison, solutions of two cationic cellulose derivatives and one cellulose betaine are used. These products are described in Section II 1. and correspond to the state of the art.

The 1% solutions of the cationic cellulose derivatives, as well as of the cellulose betaine, which was prepared as described in the Japanese publication No. 80-43 165 (Example 1), do not form a clear solution in sodium lauryl sulfate solutions. The mixtures show distinct incompatibilities, which express themselves in cloudiness and even in the formation of two separate phases. The inventive cellulose betaine, the synthesis of which is described in Section I (3a), dissolves in solutions of sodium lauryl sulfate and of coconut dimethylbenzylammonium chloride to form a clear solution.

This cellulose betaine is added to surfactant solutions of different concentration, so that the resulting solutions contain cellulose betaine at a concentration of 1%. The viscosities are determined with a Brookfield viscometer. The viscosities of the pure surfactant solutions fall within the range of 3 to 20 mPas. The results are summarized in the following Table.

| Thickening of Sodium Lauryl Sulfate Solutions | | Thickening of Coconut Dimethylbenzylammonium Chloride Solutions | |
|---|---|---|---|
| Surfactant Concentration % by weight | Viscosity 20° C. [mPas] | Surfactant Concentration % by weight | Viscosity 20° C. [mPas] |
| 1 | 60 | 1 | 28 |
| 2 | 100 | 2 | 32 |
| 5 | 140 | 5 | 36 |
| 7.5 | 200 | 7.5 | 48 |
| 10 | 250 | 10 | 60 |
| 15 | 300 | 15 | 64 |

We claim:

1. A betaine group-containing derivative of carboxymethylcellulose, wherein at least a portion of the sites normally occupied by carboxymethyl groups are occupied by betaine groups of the formula

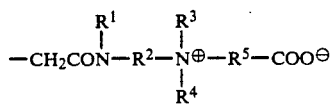

wherein
R$^1$ is hydrogen or methyl,
R$^2$ is a divalent aliphatic hydrocarbon group with 2 to 5 carbon atoms,
R$^3$ and R$^4$ are alkyl groups with 1 to 4 carbon atoms and
R$^5$ is a divalent aliphatic hydrocarbon group with 1 to 10 carbon atoms, with the proviso that, on the average, at least 0.1 betaine groups are present for each anhydroglucose unit of the polymeric molecule.

2. A derivative of carboxymethylcellulose with tertiary amino groups, wherein at least a portion of the sites normally occupied by carboxymethyl groups are occupied by groups of the formula

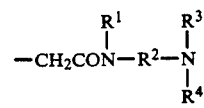

wherein
R$^1$ is hydrogen or methyl,
R$^2$ is a divalent aliphatic hydrocarbon group with 2 to 5 carbon atoms, and
R$^3$ and R$^4$ are alkyl groups with 1 to 4 carbon atoms, with the proviso that, on the average, at least 0.1 tertiary amino groups are contained per anhydroglucose unit of the polymeric molecule.

3. A method for the preparation of a betaine-group containing derivative of carboxymethylcellulose, which comprises
(a) esterifying an alkali salt of the carboxymethylcellulose at temperatures of between about 80° to 170° C., a pressure of between about 5 to 100 bar and a reaction time of between about 1 to 24 hours with, based on the carboxymethyl groups, a 1- to 10-fold molar excess of alkyl chloride, the alkyl group of which has 1 to 3 carbon atoms;
(b) removing excess alkyl chloride from the reaction mixture after the esterification;
(c) reacting the ester of the carboxymethylcellulose thus obtained with an amine of the formula

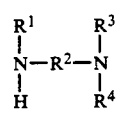

wherein
R$^1$ is hydrogen or methyl,
R$^2$ is a divalent aliphatic hydrocarbon group with 2 to 5 carbon atoms, and
R$^3$ and R$^4$ are alkyl groups with 1 to 4 carbon atoms, at temperatures of between about 80° to 150° C. and a reaction time of between about 1 to 10 hours in such amounts that 1 to 10 moles of amine are present per mole of ester group;
(d) removing after the reaction (c), excess amine from the reaction mixture, and
(e) subsequently reacting the derivative of carboxymethylcellulose-containing tertiary amino groups thus obtained at a temperature of between about 40° to 120° C. and a reaction time of between about 0.5 to 8 hours with, based on the tertiary amino groups, at least equimolar amounts of the compound X-R$^5$-COOM, in which X is a halogen group, M is an alkali ion or an ammonium ion and R$^5$ is a divalent aliphatic hydrocarbon group with 1 to 10 carbon atoms.

4. The method of claim 3, wherein step (c) is carried out at increased pressure.

5. A composition comprising an aqueous vehicle and an effective amount of the carboxymethylcellulose derivative of claim 1.

6. The composition of claim 5, wherein said effective amount of said carboxymethylcellulose derivative is between about 0.1 to 2.5% by weight.

7. A hair care preparation comprising the composition of claim 6.

8. A method of treating hair, which comprises applying to hair the composition of claim 5.

9. A method for thickening an aqueous solution or aqueous suspension comprising adding a carboxymethylcellulose derivative of claim 1 to said aqueous solution or suspension in an amount effective for the thickening thereof.

10. A method for thickening an aqueous solution of a surfactant comprising adding a carboxymethylcellulose derivative of claim 1 to said aqueous solution in an amount effective for the thickening thereof.

* * * * *